United States Patent [19]

Tischer et al.

[11] Patent Number: 5,061,640
[45] Date of Patent: Oct. 29, 1991

[54] PROCESS FOR PREPARING A CARRIER USEFUL IN IMMUNOASSAYS BY DEPOSITION OF A COMPLEX OF A SPECIFICALLY BINDING SUBSTANCE WITH HYDROPHOBIC PROTEIN, AND THE RESULTING CARRIER

[75] Inventors: Wilhelm Tischer, Peissenberg; Josef Maier, Weilheim; Rolf Deeg, Bernried, all of Fed. Rep. of Germany

[73] Assignee: Boehringer Mannheim GmbH, Mannheim, Fed. Rep. of Germany

[21] Appl. No.: 124,871

[22] Filed: Nov. 24, 1987

[30] Foreign Application Priority Data

Nov. 26, 1986 [DE] Fed. Rep. of Germany ....... 3640412

[51] Int. Cl.$^5$ ........................................... G01N 33/552
[52] U.S. Cl. ..................................... 436/527; 436/518; 436/524; 436/528; 436/530; 436/531; 436/532
[58] Field of Search ............... 436/501, 524, 528, 529, 436/530, 531, 532, 813, 824

[56] References Cited

U.S. PATENT DOCUMENTS

| | | | |
|---|---|---|---|
| 3,966,580 | 6/1976 | Janata et al. | 436/516 X |
| 4,006,059 | 2/1977 | Butler | 530/814 X |
| 4,069,352 | 1/1978 | Parsons, Jr. | 436/532 |
| 4,410,654 | 10/1983 | Cooper et al. | 436/532 X |
| 4,572,901 | 2/1986 | Ceriani et al. | |
| 4,808,530 | 2/1989 | Means et al. | 530/815 X |

FOREIGN PATENT DOCUMENTS 101912 3/1984 European Pat. Off. .
142193 5/1985 European Pat. Off. .

OTHER PUBLICATIONS

Eiji Ishikawa, et al., Enzyme-Labeling of Antibodies and Their Fragments for Enzyme Immunoassay and Immunohistochemical Staining, Journal of Immunoassay, 4(3), 209-227 (1983).

*Primary Examiner*—Sam Rosen
*Attorney, Agent, or Firm*—Felfe & Lynch

[57] ABSTRACT

The present invention provides a process for the preparation of a specifically bindable protein substance bound to an insoluble carrier material, especially for use in a heterogeneous analysis process, wherein a soluable protein with a molecular weight above about 500,000, which is more hydrophobic than the specifically bindable substance, is coupled to the specifically bindable substance and then the conjugate of reaction component and protein is adsorbed on a hydrophobic solid phase.

The present invention also provides a carrier material for use in solid phase immunoassays including a hydrophobic solid phase which is adsorbed on a conjugate of a hydrophobic protein with a molecular weight above about 500,000 and of a specifically bindable protein or protein containing substance.

16 Claims, 4 Drawing Sheets

PROCESS FOR PREPARING A CARRIER USEFUL IN IMMUNOASSAYS BY DEPOSITION OF A COMPLEX OF A SPECIFICALLY BINDING SUBSTANCE WITH HYDROPHOBIC PROTEIN, AND THE RESULTING CARRIER

The present invention is concerned with preparing a carrier useful in an immunological assay. A complex is formed of a hydrophobic protein and a member of a specifically binding pair and this complex is bound to the carrier. The invention is also concerned with the carrier produced thereby.

For the determination of a specifically bindable substance, there are frequently used processes according to the immunoassay principle. One of the components of a substance pair specifically bindable with another is thereby reacted with the receptor specific for it which is labelled in known manner. The conjugate of these two substances can then be reacted with a receptor which is specific for the conjugate or for one of the two parts of the conjugate. There are many variations for these immunological processes. It is thereby advantageous when one of the receptors is present bound to a solid phase. This makes easier the separation of reaction components present bound and non-bound. For the determination of the specifically bindable substance, one measures the amount of labelled reaction component bound to the solid phase or of labelled reaction component present in the solution and relates it in a known manner to the amount of reaction component to be determined.

In standard immunological processes, when a solid phase is used it is generally a test tube or a microtiter plate made of a synthetic material. The inner surface of these materials have reaction components fixed thereto. If spheroids are used, then the outer surfaces of these have the reaction components bound thereto. These synthetic resin test tubes, microtitre plates or spheroids usually consist of a relatively inert synthetic resin material so that the binding of the reaction component gives rise to difficulties. Furthermore, the binding of the specific reaction component to the surface in question must take place in such a manner that it does not lose the ability of specific binding to the substance specifically bindable with it. For this reason, the binding of the reactive component to the solid phase mostly takes place adsorptively.

Therefore, it has already been suggested to bring about the fixing of the reaction component to the solid phase via a coupling agent which brings about the binding. Care must thereby again be taken that the binding of the reaction component to the binding agent does not destroy the specifically reacting region of the molecule and that the reaction component is so bound that its reacting region is facing away from the solid phase and toward the complementary member of the specifically binding pair.

Furthermore, in Federal Republic of Germany Patent Specification No. 25 33 701, it is suggested, in order to achieve a better binding, to cross-link the individual immunologically effective proteins and then to absorb them on polystyrene spheroids. A further possibility given in this literature reference is simultaneously to cross-link an inert protein with the protein with immunological properties so that a cross-linked product results of inert and active protein which is then again adsorbed on polystyrene spheroids. However, depending upon chosen reaction conditions, this type of cross-linking leads to differing, non-reproducible crosslinkages with variable proportions of non-cross-linked protein, as well as of protein which has become insoluble. Furthermore, due to the differing degree of crosslinking, products result with differing binding properties.

A similar process is described in European Patent Specification No. 0,122,209 and it also displays the same disadvantages. Thus, all these known processes are still not satisfactory, still do not give an optimal adhesion of the specifically bindable substance and are of little suitability for the reproducible preparation of coated solid phases.

Therefore, it is an object of the present invention to provide a process which reproducibly improves the adhesion of the specifically bindable substance to the solid phase and provides a carrier material suitable therefor. Since many immunological processes are carried out with the addition of detergents in order to avoid turbidities, it is also an object of the present invention to improve the adhesion to such an extent that, even in the presence of detergents, the bound, specifically bindable substance is not dissolved off.

Thus, according to the present invention, there is provided a process for the preparation of a specifically bindable protein or protein containing substance bound to an insoluble carrier material, especially for use in a heterogeneous analysis process, according to the immunoassay principle, wherein a soluble protein with a molecular weight above about 500,000, which is more hydrophobic than the specifically bindable substance, is coupled to the specifically bindable substance and then the conjugate of reaction component and protein is adsorbed on a hydrophobic solid phase.

The specifically bindable substance fixed in this way to a solid phase displays an improved adhesion. The binding is also stable with regard to detergents. In the case of the production of calibration curves which are necessary for the evaluation in the case of many immunological processes, the solid phase-bound, specifically bindable substances according to the present invention give steeper calibration curves, which results in an increase of the exactitude.

A further advantage of the process according to the present invention is that it is possible to control the bound amount more exactly. Since the adhesion is significantly better than in the case of the previously known processes, the amount of specific protein which must be used is also smaller.

For the choice of soluble proteins which are suitable according to the present invention, there must be determined the molecular weight, as well as the hydrophobicity, in comparison with the corresponding value for the specifically bindable substance. The molecular weight is determined according to known methods.

A comparison of the hydrophobicity between soluble protein and specifically bindable substance can also take place by conventional methods. Suitable methods are, for example, a comparison of the fluorescent extinction after binding to coloured materials (Biochem. Biophys. Acta, 624, 13–20/1980); the elution behaviour in the case of hydrophobic chromatography (Biochem. Biophys. Acta, 576, 269–279/1979); the surface tension (Biochem. Biophys. Acta, 670, 64–73/1981); and the retention times in the case of hydrophobic interaction chromatography (HIC) (Angew. Chemie, 98, 530–548/1986; J. Chromat., 296, 107–114/1984; and Anal. Biochem., 137, 464–472/1984).

A comparison of the hydrophobicity of substances suitable according to the present invention is to be found in Sep. Sci. Technol., 14, 305–317/1979. According to that, the hydrophobicity increases, for example, in the following series: $\alpha_2$-macroglobulin (M.W. 820,000), bovine serum albumin/human serum albumin (M.W. about 70,000), egg albumin, $\alpha_2$HS-glycoprotein (M.W. about 49,000), $\beta_{1C}/\beta_{1A}$-globulin, immunoglobulin (M.W. about 150,000) and transferrin (M.W. about 90,000).

Thus, if an immunoglobulin is used as specifically bindable substance, then, for example, human serum albumin or $\alpha_2$HS-glycoprotein are not suitable as soluble proteins in the meaning of the present invention without further pre-treatment.

When human serum albumin or $\alpha_2$HS-glycoprotein is used, they must be rendered hydrophobic and must be treated to produce a polymeric molecule with a higher molecular weight. When transferrin is used, cross-linking suffices to render this substance useful in the invention. When $\alpha_2$-macroglobulin is used, the molecule only needs to be rendered hydrophobic.

Proteins which are suitable for the coupling with immunoglobulin as specifically bindable substance without pre-treatment include, for example, $\beta$-lipoproteins (M.W. about 3.2 million) and $\alpha_2$-lipoproteins (M.W. about 5–20 million).

Hydrophobing can take place, for example, by the use of heat, treatment with acids, denaturing agents and/or chaotropic ions and/or by chemical coupling with a hydrophobic compound.

Increasing of the molecular weight can take place, for example, by the use of heat, treatment with acids, denaturing agents and/or chaotropic ions and/or by cross-linking with a bi- or polyfunctional protein reagent.

The treatment is carried out until a protein polymer is obtained with a molecular weight of 500,000 or more. It is especially preferred to use a protein polymer with a molecular weight of from 500,000 to 20 million.

When cross-linking is also to take place, the hydrophobing can be carried out before, during or after the cross-linking but not in the presence of the specifically bindable substance.

For hydrophobing by heating, one usually uses temperatures of from 40 to 95° C. over a period of time of 1 minute to 10 hours, for example as described in Biochem. Biophys. Acta, 624, 13–20/1980.

As acids, there are used, for example, acetic acid, propionic acid, lactic acid or hydrochloric acid. The usual concentrations are 1 to 100 mMole/liter with a period of action of from 10 minutes to 16 hours.

Suitable chaotropic ions include, for example, thiocyanates, iodides, fluorides, bromides, perchlorates and sulphates. Suitable denaturing agents include, for example, guanidine hydrochloride and urea. Concentrations of 10 mMole/liter to 6 mole/liter are usually here used.

For the derivatisation of hydrophobic compounds, there are preferably used soluble fatty acids, lipoids in low and high molecular weight form, as well as synthetic polymers, such as polypropylene glycol, or soluble copolymers of polystyrene. The derivatisation takes place according to well known methods.

Cross-linking by way of bi- and polyfunctional compounds is carried out with known protein binding reagents. These are compounds which contain at least two functional groups, which can be the same or different and can react via these functional groups with functional groups of proteins. Compounds are preferably used which consist of an alkyl chain on the ends of which are present, for example, succinimide, maleinimide and/or aldehyde groups.

The protein is cross-linked in the usual manner with the bi- or polyfunctional compounds by reacting together the soluble protein and the bi- or polyfunctional compound.

For hydrophobing and/or cross-linking, there are preferably used precursor proteins with a molecular weight of from 10,000 to 700,000, bovine serum albumin, lipase and immune $\gamma$-globulin being especially preferred.

The specifically bindable protein substance to be bound is then coupled to the protein in known manner. Suitable coupling methods are described, for example, by Ishikawa in J. Immunoassay, 4, 209–327/1983. Proteins such as antibodies, antibody fragments, antigens and haptens can be used as specifically bindable substances.

The conjugate obtained of specifically bindable protein substance and protein is then adsorbed adsorptively on the synthetic resin surface serving as solid phase. The adsorptive binding to the solid phase takes place via strong and weak exchange actions, hydrophobic forces, dipole-dipole and ion-dipole interactions. As hydrophobic solid phases, there can be used carrier materials with a surface tension which is smaller than the surface tension of the hydrophobic soluble protein, i.e. are more hydrophobic than protein. Carrier materials with a surface tension of $<40$ erg/cm$^2$ are preferably used. Polystyrene, polymethacrylate, polytetrafluoroethylene (Teflon), polyamide, copolymers of styrene and acrylonitrile, glass and cellulose products are especially preferred. They can be present in any desired form, for instance, in the form of a film, plate, powder, granules or fibre fleece, preferably in the form of a glass fibre fleece or a fleece from cellulose-/cellulose ester fibres and polymer fibres.

Hydrophobed proteins display an especially good adsorptive binding. Due to the hydrophobing, intramolecular bridge bonds of the protein are possibly opened so that hydrophobic parts of the protein reach the surface and there better adhere to the hydrophobic synthetic resin surface than the hydrophilic parts which are particularly to be found on the surface in the non-hydrophobed protein.

The process according to the present invention can be used for the determination of a specifically bindable substance. As substance pairs, one reaction component of which is present bound to the solid phase, there can be used, for example, antigen-antibody, hapten-antibody and other proteins capable of specific binding to one another, such as, in particular, the system streptavidin or avidin and biotin, which is preferred.

Before the conjugate of protein and specifically bindable substance is adsorbed on to the hydrophobic solid phase, it is also possible to pre-treat the solid phase physically or chemically. Thus, for example, a synthetic resin surface can be pre-swollen or activated in some other known way.

The carrier material according to the present invention for use in solid phase immunoassay is characterised in that it consists of a hydrophobic solid phase on which is adsorbed a protein with a molecular weight of above about 500,000 to which is bound a specifically bindable substance.

This carrier material is outstandingly suitable for use in solid phase immunoassays since the specifically bindable substance adheres very well and is also not desorbed in the case of the addition of detergents.

The carrier material is used, for example, in the form of test tubes, microtitre plates or spheroids which are coated with a cross-linked protein to which is bound a specifically bindable substance.

On the solid base is adsorbed a conjugate consisting of a cross-linked protein and a specifically bindable substance. The protein is preferably bovine serum albumin, lipase or an immune γ-globulin which has been cross-linked in the described manner.

According to the present invention, there is provided a process and a carrier material in order to fix a specifically bindable substance with good adhesion and longlastingly to a hydrophobic solid phase. The adhesion could thus be improved to such an extent that even an addition of detergents does not lead to a dissolving off of the substance. The process according to the present invention is also simple to carry out.

The present invention will now be described in more detail in the following Examples, reference thereby being made to the accompanying drawings, in which:

FIG. 1 is a calibration curve for a TSH determination with the use of non-crosslinked Fab <TSH> (curve 1), crosslinked Fab <TSH> (curve 2), conjugate of Fab <TSH>/β-Gal (curve 3) and conjugate of Fab <TSH>/thermo-BSA (curve 4) in Luran test tubes;

FIG. 2 is a calibration curve for a TSH determination with the use of immobilised streptavidin and biotinylated Ak <TSH>; non-crosslinked streptavidin (curve 1), crosslinked streptavidin (curve 2), streptavidin/β-gal conjugate (curve 3), streptavidin/BSA conjugate (curve 4), streptavidin/thermo-BSA conjugate (curve 5) and streptavidin/thermo-BSA conjugate (curve 6); in the case of curves 1 to 5, the solid phases are Luran test tubes and in the case of curve 6 the solid phases are polystyrene test tubes;

EXAMPLE 1

Figure 1:
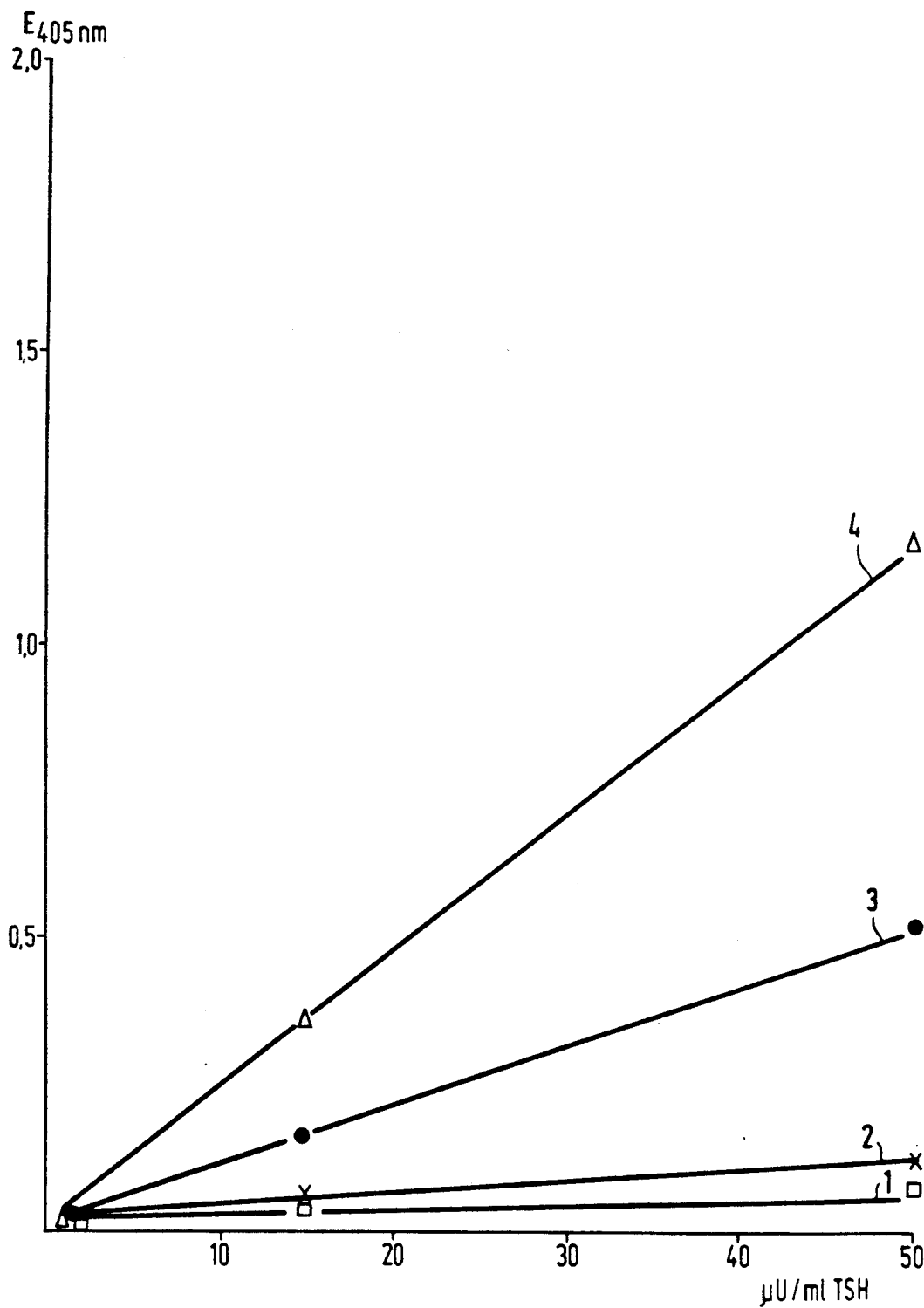

Binding of Fab Fragments of a Monoclonal Antibody Against TSH to Polystyrene Test Tubes a) Preparation of Fab Fragments (Fab <TSH>)

Monoclonal antibodies (MAB <TSH>) are obtained by the method described by Galfre and Millstein (Meth. in Enzymology, 73/1981). For further purification, the ascites liquid is subjected to an ammonium sulphate precipitation and to a passage over DEAE-cellulose.

A papain fission is subsequently carried out by the method described in Biochem. J., 73, 119–126/1959. The Fab fragments hereby formed are separated from the non-digested IgG molecules and the Fc fragments by means of gel filtration over Sephadex G100 and ion exchanger chromatography over DEAE-cellulose according to Meth. in Enzymology, 73, 418–459/1081.

b) Crosslinking of the Fab Fragments Without Protein Addition (Comparison)

50 mg. of Fab fragments are dissolved in 2 ml. 0.05 mole/liter potassium phosphate buffer (pH 7.5) and 0.4 ml. disuccinimidyl suberate (manufacturer Pierce) dissolved in dioxan (7.4 mg./ml.) is added thereto, with stirring. After incubating for 2 hours at 25° C., the reaction is broken off by the addition of 0.2 ml. of 0.1 mole/liter lysine hydrochloride. The reaction batch is diluted with 0.2 ml. potassium phosphate buffer (v. supra) and centrifuged. The supernatant is desalinated over an Ultrogel AcA 202 column (LKB, Gräfelfing, Federal Republic of Germany), 11.3 ml. being obtained with 45 mg. of protein. A part of this preparation is fractionated on a Superose-6-column (Deutsche Pharmacia GmbH) at a flowthrough rate of 0.5 ml./minute in 0.05 mole/liter potassium phosphate buffer (pH 7.0) and the fractions with a molecular weight of about 500,000 to 5 million are further used.

c) Crosslinking of the Fab Fragments with Untreated γ-Globulin (Comparison)

Fab fragments and bovine γ-globulin (Serva, Heidelberg, Federal Republic of Germany) are mixed in a weight ratio of 1:1. The crosslinking is carried out as described under b).

d) Binding of Fab Fragments to Pre-Crosslinked γ-Globulin (According to the Present Invention)

1.25 g. γ-globulin are dissolved in 10 ml. of 0.05 mole/liter potassium phosphate buffer (pH 7.8) and centrifuged clear in a Sorvall cooled centrifuge for 10 minutes at 5000 r.p.m. 1.75 ml. Disuccinimidyl suberate are added to this solution which is then diluted with 2.5 ml. water. After stirring for 4 hours at 25° C., 10 ml. of 0.1 liter lysine are added thereto and the pH value adjusted to 6.8 and centrifuged. The supernatant is separated on a preparative gel filtration column (TSK 3000, LKB Grafelfing, Federal Republic of Germany), concentrated by ultrafiltration and stored at 4° C.

50 mg. of this crosslinked γ-globulin are dissolved in 5 ml. of 0.05 mole/liter potassium phosphate buffer and the pH value adjusted to 9.5 by the addition of solid sodium carbonate. 50 mg. N-acetylhomocysteine thiolacetone (Serva, Heidelberg, Federal Republic of Germany) are then added thereto and stirred for 5 hours at 25° C., while gassing with nitrogen. The batch is subsequently desalinated over an Ultragel AcA 202 column in a buffer of 0.1 mole/liter potassium phosphate (pH 7.0), 0.001 mole/liter magnesium chloride and 0.05 mole/liter sodium chloride.

Fab fragments prepared according to a) (10 mg. in 1 ml. of 0.01 mole/liter potassium phosphate buffer (pH 7.0)) are activated with 0.002 ml. maleinimidohexanoyl-N-hydroxysuccinimide ester (Boehringer Mannheim GmbH) in dimethyl sulphoxide (33 mg./ml.) for 2 hours at 25° C., subsequently centrifuged and desalinated over an AcA 202 column.

These fragments are subsequently combined with the γ-globulin (weight ratio of the proteins 1:1) and incubated for 1 hour at 25° C. and at pH 7.0. Subsequently, it is dialysed against desalinated water overnight at 4° C. and at a protein concentration of 2.5 mg./ml.

This conjugate can be used directly for the adsorption on to a solid phase.

e) Preparation of Fab Fragments Coupled to Thermo-BSA (According to the Present Invention)

1 g. BSA-I is dissolved in 100 ml. of 50 mMole/liter potassium phosphate (pH 7.0), heated to 70° C. and kept at this temperature for 4 hours, with gentle stirring. The solution is cooled, filtered and adjusted in an ultrafiltration cell (exclusion limit: 30,000 Dalton) to a concentration of 50 mg./ml. Subsequently, it is dialysed against a 30 fold volume of double distilled water and subsequently lyophilised. The product has a molecular weight of about 700,000.

Before coupling to the Fab fragments, the thermo-BSA is activated. For this purpose, 68 mg. thermo-BSA are dissolved in 2 ml. 0.1 mole/liter potassium phosphate (pH 7.8) and slowly mixed with a solution of 3.8 mg. S-acetylmercaptosuccinic acid anhydride (SAMSA). After a reaction time of 3 hours, it is dialysed against 2 litres of 50 mMole/liter potassium phosphate (pH 6.5). This thermo-BSA is incubated for 1 hour at 25° C. and pH 7.0 with the Fab fragments activated according to d) in a weight ratio of 1:1, and subsequently dialysed against desalinated water overnight at 4° C. and at a protein concentration of 2.5 mg./ml. This product is used directly for the coating.

f) Preparation of Fab Fragments Coupled to β-galactosidase (According to the Present Invention)

Fab fragments are activated as described in d) and coupled to the SH groups of β-galactosidase according to J. Immunoassay, 4, 209–327/1983. The β-galactosidase used has a molecular weight of 500,000 to 2 million. For another experiment, there is used crosslinked β-galactosidase (M.W. about 5 million).

g) Loading of Polystyrene Test Tubes with Fab Fragments or Conjuqates Thereof 50 mg. of a lyophilisate of the Fab fragment or of the conjugate are dissolved in 10 ml. double distilled water. 1 ml. of this solution is diluted in 1000 ml. of a loading buffer of 5.25 g./liter sodium dihydrogen phosphate and 1 g./liter sodium azide and stirred for 30 minutes at ambient temperature.

Test tubes of polystyrene or Luran (manufacturer BASF) are each filled with 1.5 ml. of the solution and loaded overnight (about 22 hours). Thereafter, the test tubes are completely emptied and the function test described hereinafter is carried out.

h) Function Test Via TSH Determination

The polystyrene and Luran test tubes loaded according to g) are used in a TSH determination reagent analogously to TSH-Enzymun test (Boehringer Mannheim GmbH, order No. 736 082) and a calibration curve measured according to the test procedure. There are hereby obtained the measurement values shown in the following Table 1 and in FIG. 1 of the accompanying drawings.

It can be seen (FIG. 1) that with Fab fragments which have been immobilised without the addition of protein, only a very flat calibration can be obtained (curves 1 and 2). By coupling to proteins with a molecular weight below 500,000 and low hydrophobicity, the calibration curve (curve 3) is somewhat steeper but satisfactory results still cannot be achieved. On the other hand, with the conjugates prepared according to the present invention, there can be achieved a sufficiently steep calibration curve (curve 4).

TABLE 1

Standard values for various Fab <TSH> conjugates

| conjugate* | hydrophobicity of the protein** | M.W. of the protein | measurement signal of TSH standard in mE/ml. 0.1 μU TSH[1] | 12.5 μU TSH[2] |
|---|---|---|---|---|
| Fab <TSH> | — | — | 102 | 107 |
| crosslinked Fab <TSH> without protein (Example 16) | — | — | 126 | 134 |
| Fab <TSH>/β-Gal (Example 1f) | 39.6 | 500,000 | 110 | 260 |
| crosslinked Fab <TSH>/β-Gal (Example 1f) | 40.2 | 5 million | 110 | 260 |
| Fab <TSH>/γ-globulin (Example 1c) | 32.0 | 150,000 | 117 | 253 |
| Fab <TSH>/γ-globulin (example 1d) | not elutable | 5 million | 75 | 480 |

*total amount of protein in the case of adsorption: 1.5 ml. with 5 μg./ml. of protein per test tube
**Tp [min], cf. Example 3
[1]lowest value of a measurement curve (should be as low as possible)
[2]highest value of a measurement curve (should be as high as possible)

EXAMPLE 2

Immobilisation of Streptavidin a) Preparation of Crosslinked Streptavidin

Streptavidin (manufacturer Boehringer Mannheim GmbH) is crosslinked analogously to Example 1b.

b) Preparation of Streptavidin Bound to BSA or to β-galactosidase

The binding to non-crosslinked BSA or to β-galactosidase takes place analogously to Example 1f.

c) Preparation of Streptavidin Coupled to Thermo-BSA

Activation of Streptavidin 60 mg. Streptavidin are dissolved in 6 ml. of 50 mMole/liter potassium phosphate/100 mMole/liter sodium chloride (pH 7.0) and stored at 4° C. 6.16 mg. maleinimidohexanoyl-N-hydroxysuccinimide ester are dissolved in 620 μl. dioxan and stirred into the streptavidin solution. After a reaction time of 2 hours at 4° C., it is dialysed twice against 1 liter of 50 mMole/liter potassium phosphate/100 mMole/liter sodium chloride (pH 5) at 4° C.

Preparation of a Conjugate of Streptavidin and Thermo-BSA 66 mg. Streptavidin are dissolved in 10 ml. of 50 mMole/liter potassium phosphate (pH 5.0) and 100 mMole/liter sodium chloride and 72 mg. of activated thermo-BSA-SAMBA (preparation according to Example 1e) in 5 ml. of 50 mMole/liter potassium phosphate/100 mMole/liter sodium chloride (pH 6.5) are added thereto. After mixing, 50 μl. of 1 mole/liter hydroxylamine (pH 7.0) are added thereto in order to stop the reaction. After 3 hours, the reaction product is purified via gel chromatography (Superose 6, 50 mMole/liter potassium phosphate/100 mMole/liter sodium chloride; pH pb 7.5). There is obtained a conjugate with a molecular weight of from 1 to 5 million.

d) Loading of Polystyrene and Luran Test Tubes with Streptavidin or Streptavidin Conjuqate The loading takes place in the manner describes in Example 1g).

e) Measurement of Standard Values Via a TSH Determination

The test tubes loaded according to d) are used in a TSH Enzymun reagent (4 fold conjugate activity). However, in variation of the there-described procedure, instead of the immobilised antibody, there is used a biotinylated MAB <TSH>. The preparation of this biotinylated MAB takes place according to J.A.C.S., 100, 3585–3590/1978. The antibody is used in the test in a concentration of 400 ng. per test tube, together with the other reagents.

Figure 2:
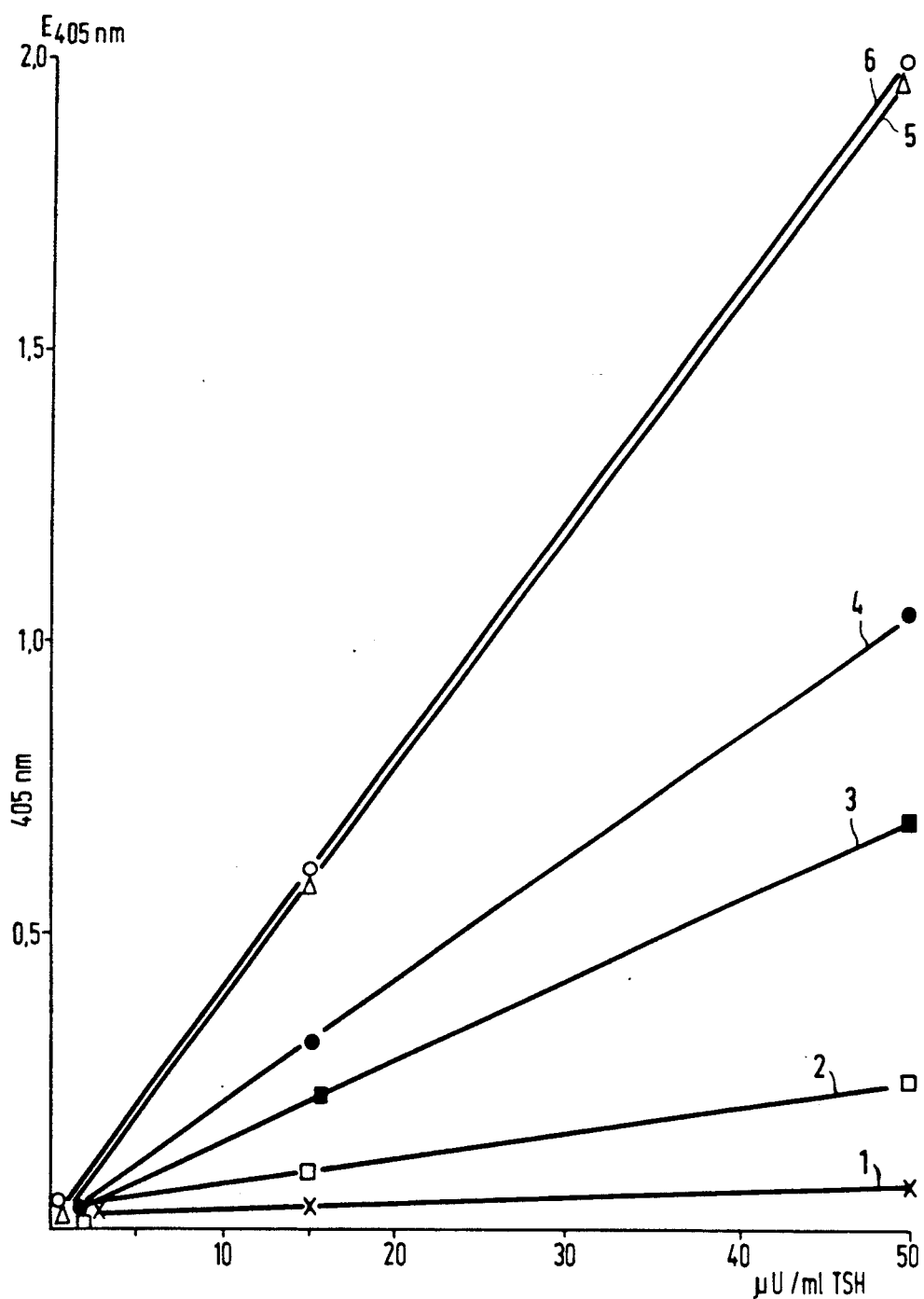

The results obtained are shown in FIG. 2. It can be seen therefrom that, with increasing molecular weight and with increasing hydrophobicity, the gradient of the calibration curve and thus of the achievable exactitude increases.

EXAMPLE 3

Figure 3:
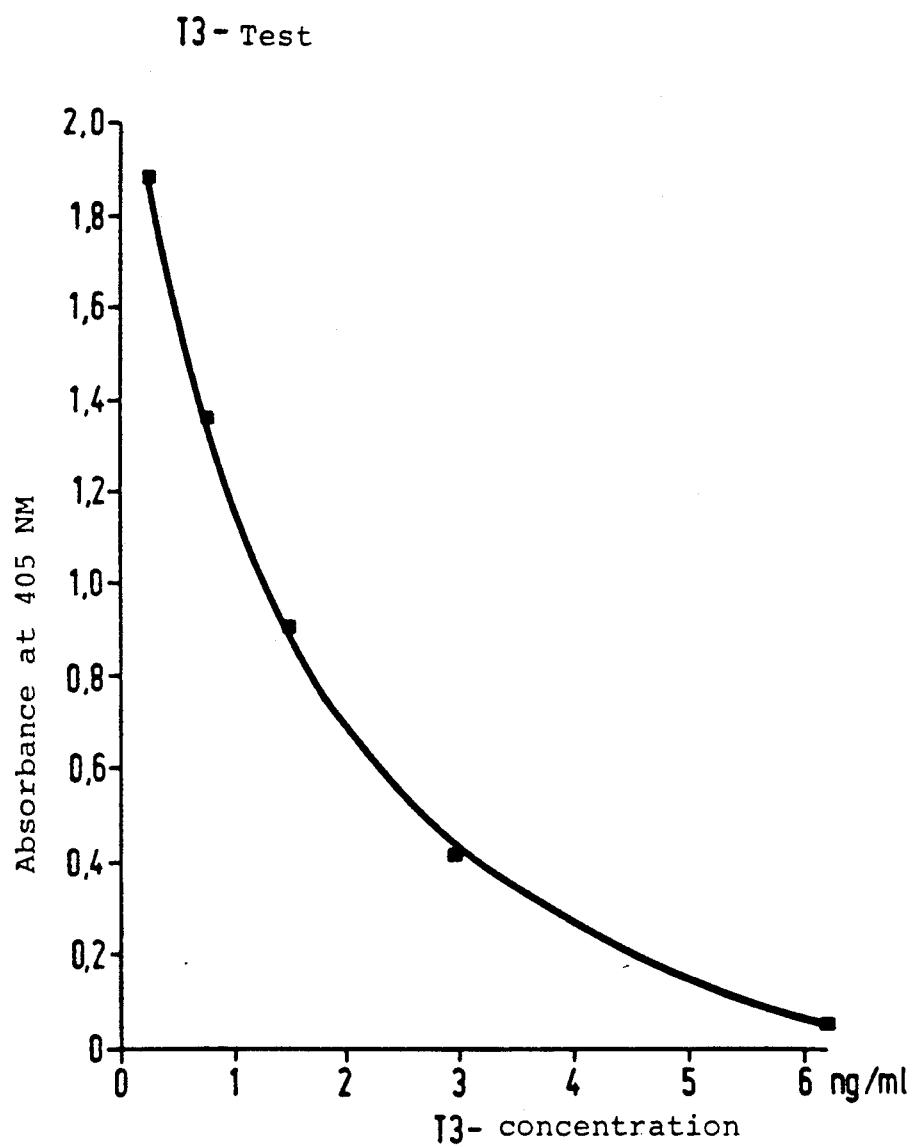
FIG. 3 is a calibration curve for a T3 test.

A T3 test is carried out with the test tubes loaded according to the present invention. For this purpose, 200 μl. of sample or of standard solution are preincubated together with 500 μl. of a polyclonal antibody conjugate against T3, which is labelled with POD, in a test tube which had been coated with streptavidin coupled to thermo-BSA. After 5 minutes, 400 ng. of polymerised T3 biotinylated in known manner are incubated for 30 minutes in 500 μl. of buffer. As buffer, there is used a solution of sodium hydrogen phosphate with a pH of 8.65 which contains 0.20% BSA and 0.04% 8-anilino-1-naphthalenesulphonic acid (ANA). After incubation, washing is carried out three times and subsequently 1 ml. ABTS substrate solution is added thereto. After further incubation for 30 minutes, measurement is then carried out at 405 nm in a photometer. The measurement values obtained are given in the curve shown in FIG. 3.

EXAMPLE 4

Figure 4:
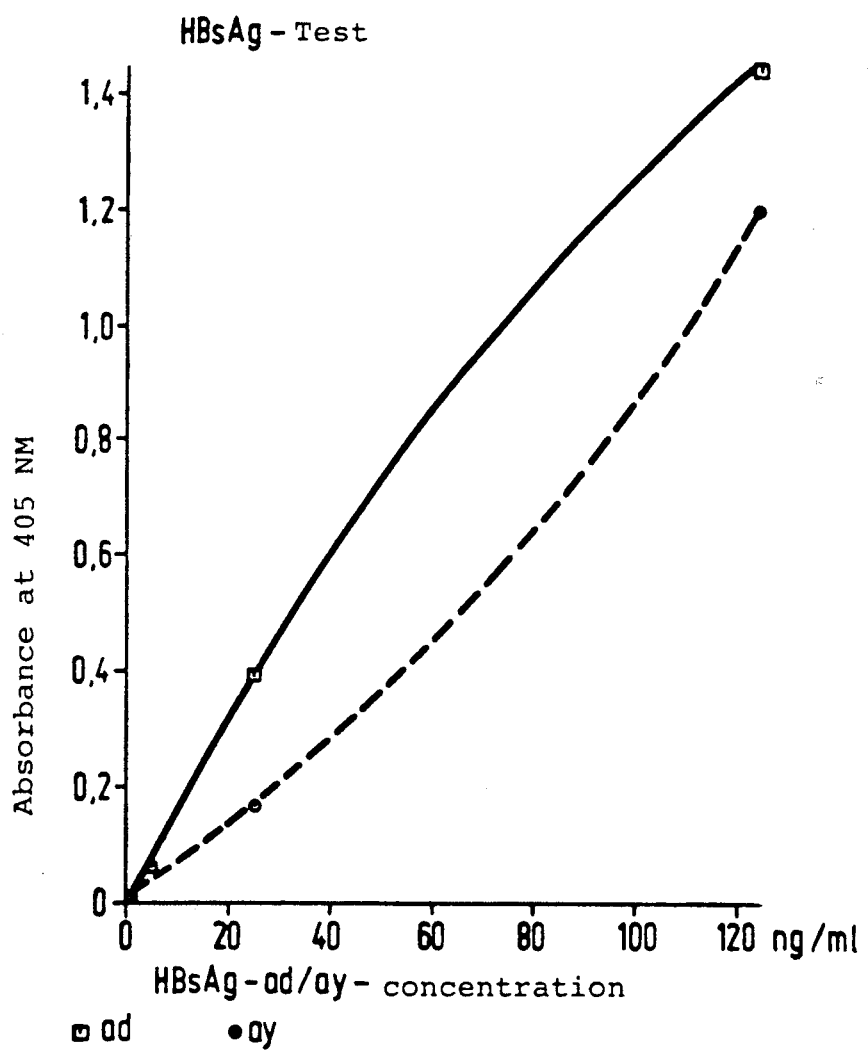
FIG. 4 is a calibration curve for an HBs AG test.

An HBsAg test is carried out with test tubes coated according to the present invention. For this purpose, in a test tube coated according to Example 1g), there are simultaneously dissolved 400 ng. biotinylated monoclonal antibody against HBs-antigen and 50 mU of the same antibody which are labelled with POD and 1 ml. of the buffer of the same composition as described in Example 3 added thereto, together with 200 μl. of standard solution. As standard solution, there is added, on the one hand, purified HBsAg sub-type ay and, on the other hand, purified HBsAg sub-type ad. Incubation is then carried out for 4 hours at ambient temperature. After washing the test tubes three times, 1 ml. ABTS substrate solution is added thereto. After 20 minutes, the reaction is substantially ended and the extinction is measured at 405 nm in a photometer. The measurement values are to be seen from FIG. 4, in which the unbroken curve gives the values for HBsAg sub-type ad and the broken curve gives the values for HBsAg sub-type ay.

EXAMPLE 5

The dissolving off of the test tubes coated according to the present invention is compared with test tubes coated according to known processes. For this purpose, on the one hand, test tubes are loaded with 1.5 ml. of a streptavidin-thermo-BSA solution (4 μg./ml.) in 40 mM sodium hydrogen phosphate buffer (pH 7.4) at 20° C. for 18 to 24 hours. After sucking out the test tubes, there takes place an after-treatment with 1.8 ml. of a 2% saccharose solution which contains 0.9% sodium chloride and 0.3% BSA, the after-treatment being carried out for 30 minutes at 20° C. Subsequently, the test tubes are dried for 24 hours at 20° C. and 40% relative humidity. These test tubes are ready for use for carrying out tests. Furthermore, test tubes are loaded in known manner with streptavidin. The dissolving off behaviour in the case of the action of detergents is tested with these test tubes. The results obtained are given in the following Table 2:

TABLE 2

| test tube loading | material | % dissolving off 1% Pluronic F 68 (30 min., RT) | % dissolving off 0.5% Triton (30 min., RT) | % dissolving off function test (30 min., 20° C.) | % dissolving off function test (30 min., 30° C.) |
|---|---|---|---|---|---|
| Streptavidin (comparison) | Luran | 13.9 | 42 | 17.8 | 28 |
|  | polystyrene | 11 | 25 | 9.6 | 11.6 |
| thermo-BSA-streptavidin (according to the present invention) | Luran | 2.1 | 8 | 3.1 | 11.6 |
|  | polystyrene | 1.5 | 2.1 | 1.6 | 1.7 |

RT = ambient temperature

The per cent dissolving off is determined according to the methods known to the skilled worker, for example, by $^{125}F$-labelling of streptavidin and streptavidin-thermo-BSA or by an enzymatic determination.

For the enzymatic determination of the per cent dissolving off, the coated test tubes are incubated with 50 mMole/liter potassium phosphate buffer, pH 7.0, to which a detergent according to Table II was added, under the conditions according to Table II.

Subsequently, incubation is carried out at ambient for one hour, washing takes place with the above-mentioned buffer, and incubation is carried out with a conjugate of biotin POD (200 mU/ml. POD activity) for one hour at ambient, washing takes place, and 2 ml ABTS ® solution is added thereto (Example 7). After substrate reaction for one hour, the extinction is measured at 405 nm, and from this the per cent dissolving off of streptavidin and streptavidin-thermo-BSA is determined via a standard calibration curve.

EXAMPLE 6

Determination of the Hydrophobicity of Proteins with Hydrophobic Interaction Chromatoqraphy (HIC)

The hydrophobicity of various compounds is investigated with a liquid chromatograph (Hewlett Packard 1090 LUSI). The pre-column is a BioRad Biogel TSK-phenyl-5PW column (length 5 mm. × internal diameter 4.6 mm.). Column: BioRad-Biogel TSK-phenyl-5PW (length 75 mm. × internal diameter 7.5 mm., 10 μm. 1000 Å). as detector, there is used a Hitachi F 1000 fluorimeter. Eluents/gradient (see Table 3).

a. 1.5 mol/liter ammonium sulphate solution in 1/100 mole/liter monopotassium dihydrogen phosphate buffer (pH 6.8)

b 1/100 mole/liter monopotassium dihydrogen phosphate buffer (ph 6.8).

TABLE 3

| a (%) | b (%) | minutes retention time |
|-------|-------|------------------------|
| 100   | 0     | 0                      |
| 100   | 0     | 5                      |
| 0     | 100   | 30 flow - 0.5 min.     |
| 0     | 100   | 5                      |
| 100   | 0     | 5                      |
| 100   | 0     | 5                      |

Working temperature: cold chamber +7° C.

Sample preparation:

The samples are used undiluted. The sample volume is 10 μl.

The compounds to be investigated are dissolved at a concentration of 0.2 to 1.4 mg./ml. in 10 mMole/liter potassium phosphate buffer (pH 6.8).

The following Table 4 summarises the retention times for various proteins and specifically bindable substances. The longer is the retention time, the greater is the hydrophobicity.

TABLE 4

| protein | retention time $t_p$ (min.) |
|---------|------------------------------|
| Fab TSH | 41.5 |
| BSA | 23.2 |
| γ-globulin | 32.0 |
| β-galactosidase | 39.6 |
| crosslinked β-galactosidase | 40.2 |
| streptavidin | 38.3 |
| thermo-BSA (Example 1e) | not elutable |
| γ-globulin, crosslinked (Example 1a) | not elutable |

The proteins which are not elutable under there conditions are especially suitable and are preferably used, thermo-BSA being quite especially preferred.

EXAMPLE 7

Adsorption of Thermo-BSA-Streptavidin on Glass Fibre Fleece

A glass fibre fleece (6 × 6 mm.) is soaked in its absorption volume (ca. 30 μl.), with a solution of 30 μg/ml. thermo-BSA-streptavidin (prepared according to Example 2c) in 50 nMole/liter potassium phosphate buffer, pH 7.0, and dried at 50° C. in circulating drier.

For determining the biotin binding capacity, the strip is soaked with 30 μl. of a reagent consisting of a conjugate of peroxidase (POD) and biotin and having a POD activity of 50 mU/ml., biotin standard with concentrations of 0.5, 10, 20, 30, 40, 50, 100, 200, 1000 ng/ml. biotin, and incubated for 2 minutes. Thereafter, 2 % o-Tween-20 washing is carried out once with a surplus of 50 mMole/liter potassium phosphate buffer, pH 7.0, and subsequently 100 mMole/liter citrate buffer, pH 4.4; 3.2 mMole/liter perborate; 1.9 mole/liter ABTS (2,2'-azino-di[3-ethyl-benzthiazolinesulphonic acid(6)] -diammonium salt are introduced in 2 ml. ABTS solution and agitated for 15 minutes. After substrate reaction for 1 hour, the extinction is measured at 405 nm., and from this the biotin binding capacity is determined via the semimaximum signal drop.

We claim:

1. A process for preparing an insoluble carrier material useful in binding assays comprising;

forming a cross-linked conjugate of a water-soluble first protein having a molecular weight of at least 500,000 daltons with a second protein substance which conjugates by cross-linking with the water-soluble first protein wherein the water-soluble first protein is more hydrophobic than said second protein substance, adsorbing the cross-linked conjugate on a hydrophobic solid phase material to form said insoluble carrier material, wherein the second protein substance consists of one member of a specifically bindable pair of substances wherein the binding member is other than the water-soluble protein so that the cross-linked conjugate is specifically bindable.

2. The process according to claim 1, wherein said water-soluble protein has a molecular weight in the range of 500,000 to 20 million daltons.

3. The process according to claim 1, and further including the step of preparing said water-soluble protein prior to the forming of said cross-linked conjugate, the preparing of said water-soluble protein including linking a precursor protein having an original molecular weight in the range of 10,000 to 700,000 daltons with at least one other molecule to form a molecule having a molecular weight greater than the molecular weight of the precursor protein and in the range of 500,000 to 20 million daltons.

4. The process according to claim 3 and the linking of said precursor protein including cross-linking said precursor protein prior to conjugation with one or more reagents selected from the group consisting of bifunctional protein reagents and polyfunctional protein reagents.

5. The process according to claim 1 and further including the step of preparing said water-soluble protein from a precursor protein prior to forming the cross-linked conjugate, said preparing of said water-soluble protein including a step of causing the precursor protein to become more hydrophobic.

6. The process according to claim 5 and the step of causing the precursor protein to become more hydrophobic being accomplished by a method selected from the group consisting of heat treatment, treatment with acid, treatment with denaturing agents, treatment with chaotropic ions, and treatment to cause chemical coupling with a hydrophobic compound.

7. The process according to claim 4, and the cross-linking of the precursor protein including cross-linking with disuccinimidyl suberate.

8. The process according to claim 3, and said precursor protein being selected from the group consisting of bovine serum albumin, lipase, and immune γ-globulin.

9. The process of claim 1 wherein the binding assay is an immunoassay.

10. A specifically bindable complex adapted for adsorption onto a hydrophobic solid phase, said complex comprising:
a water-soluble first protein coupled with a second protein substance to form a cross-linked conjugate therewith wherein said second protein is one of a binding pair of substances which specifically bind with each other and which conjugate is specifically bindable with the other substance of the binding pair, said soluble first protein having a molecular weight of at least about 500,000 daltons and being more hydrophobic than said second protein substance.

11. A carrier material comprising:
a hydrophobic solid phase; and
a crook-linked conjugate being absorbedly supported on said solid phase said cross-linked conjugate comprising
a water-soluble hydrophobic first protein having a molecular weight of at least about 500,000 daltons and being coupled with a second protein substance to form said cross-linked conjugate, wherein the second protein is one of a binding pair of substances which specifically bind with each other and said cross-linked conjugate is specifically bindable with the other substance of the binding pair of substances.

12. The carrier material according to claim 11, wherein said hydrophobic solid phase is of a material selected from the group consisting of polystyrene, polymethacrylate, polyamide, polytetrafluoroethylene, and copolymers of styrene and acrylonitrile.

13. The carrier material according to claim 11, and said hydrophobic protein being derived from a precursor protein selected from the group consisting of bovine serum albumin, lipase, and immune ↓-globulin, which precursor protein is treated to increase the molecular weight and the hydrophobic quality of said precursor protein.

14. The carrier material of claim 11 wherein the second protein substance is selected from the group consisting of antigens, and fragments thereof.

15. The carrier material of claim 11, wherein the second protein substance is selected from the group consisting of streptavidin and avidin.

16. The carrier material of claim 11 wherein said solid phase is a fleece containing material selected from the group consisting of
glass fibers, and
mixtures of polymer fibers and fibers of cellulose or cellulose ester.

* * * * *